United States Patent [19]

Bell

[11] Patent Number: 5,181,908
[45] Date of Patent: Jan. 26, 1993

[54] METHOD AND APPARATUS FOR LAVAGING WITH OXYGENATED IRRIGATING FLUID WHILE SUCTIONING

[75] Inventor: Craig J. Bell, Winchester, N.H.

[73] Assignee: Smiths Industries Medical Systems Inc., Keene, N.H.

[21] Appl. No.: 624,238

[22] Filed: Dec. 7, 1990

[51] Int. Cl.⁵ .............................................. A61M 37/00
[52] U.S. Cl. ........................................ 604/24; 604/28; 604/147; 604/149
[58] Field of Search ............... 604/149, 147, 146, 145, 604/28, 24

[56] References Cited

U.S. PATENT DOCUMENTS

| | | | |
|---|---|---|---|
| 3,516,405 | 6/1970 | Hopper | 604/149 |
| 3,628,532 | 12/1971 | Magrath | 604/149 X |
| 3,810,471 | 5/1974 | Truhan . | |
| 4,327,721 | 5/1982 | Goldin et al. . | |
| 4,508,533 | 5/1985 | Abramson . | |
| 4,657,532 | 4/1987 | Osterholm | 604/24 |
| 4,692,139 | 9/1987 | Stiles | 604/22 |
| 4,705,073 | 11/1987 | Beck . | |
| 4,836,199 | 6/1989 | Palmer | 604/163 X |
| 4,903,688 | 2/1990 | Bibby et al. . | |
| 4,955,375 | 9/1990 | Martinez . | |
| 5,029,580 | 7/1991 | Radford et al. . | |
| 5,033,466 | 7/1991 | Weymuller, Jr. . | |

Primary Examiner—John J. Wilson
Assistant Examiner—Jeffrey A. Smith

[57] ABSTRACT

A suction catheter and method of using same in which oxygenated irrigating fluid is provided to the suctioning site. The oxygenated fluid can be formed using a Y-connector to mix oxygen and fluid in a single conduit, a reservoir of fluid having oxygen bubbled into it, or through the use of an oxygen exchanger. Pressurized oxygen-containing gas may be fed to the Y-connector to force the gas and irrigating fluid out through the catheter. The suction may be a dual lumen catheter or a tube within a tube.

8 Claims, 2 Drawing Sheets

METHOD AND APPARATUS FOR LAVAGING WITH OXYGENATED IRRIGATING FLUID WHILE SUCTIONING

BACKGROUND OF THE INVENTION

The present invention is directed to a suction catheter suitable for use in removing undesirable fluids and debris from a patient. In particular, the present invention is concerned with a fluid supplied by a suction catheter to a patient for lavage purposes.

Closed ventilation suction catheter systems, such as that available under the trade designation of STERI-CATH, Model No. 6100 available from Smiths Industries Medical Systems, Inc. (SIMS), the assignee of the present invention, are presently in wide use. The closed ventilation suction catheter system includes a catheter tube, a cross piece connecting member for connection to an endotracheal tube and also for connection to a ventilating apparatus, a vacuum connection member located at the end of a suction control valve opposite to that nearest the patient, and a protective sleeve located between the cross piece and the suction control valve. Closed ventilation suction catheter systems make it possible to continue ventilation while at the same time applying suction to remove undesired accumulated fluid from a patient.

In addition, in removing fluid from a patient, it sometimes becomes necessary to provide a lavage solution to the patient, especially when tenacious mucous has built up. To accomplish this, the STERICATH Model No. 6100, catheter included a dual lumen catheter tube and an irrigation port located at the vacuum connection member whereby lavage solution could be conveyed through the second lumen of the catheter. The suctioning process unfortunately can cause oxygen desaturation of the patient.

It is an object of the present invention to substantially reduce or eliminate the oxygen desaturation during suctioning while using an irrigating fluid for lavage.

U.S. Pat. No. 4,705,073 (Beck) discloses a plastic gate valve for use in conjunction with a suction catheter. The valve is used in a system which alternates between oxygenating the lungs of a patient and removing fluid therefrom by suction. The valve permits a saline solution to be injected along with the administration of oxygen, while the suction is switched off. U.S Pat. No. 3,628,532 (Magrath) discloses an aspiration and respiration apparatus in which liquid may be injected from a container or a syringe. The liquid line is the same line used for pressurized oxygen being supplied to an air breathing vertebrate. The liquid may be used to counteract the drying effects otherwise encountered by the pressurized oxygen. In the Magrath device, moisturized gas can be formed from condensate on the inner surface of a mask.

SUMMARY OF THE INVENTION

The present invention is directed to a method and apparatus for dislodging and suctioning debris with a suction catheter without causing undue oxygen desaturation.

In accordance with the present invention, a multilumen suction catheter is inserted into, for example, the trachea of a patient. Oxygen is mixed with an irrigating fluid to produce oxygenated irrigating fluid. The oxygenated irrigating fluid is delivered through a first lumen of the multilumen suction catheter into the trachea so as to dislodge debris. Suction is provided through a second lumen to remove dislodged debris and irrigating fluid from the trachea. This method advantageously derives the benefits from the use of irrigating fluid to dislodge debris and yet avoids the problem of oxygen desaturation.

The suction catheter of the present invention includes a tube which can be inserted into the patient. The tube includes a primary conduit for removing fluid from the patient and a secondary conduit for providing irrigating fluid. A cross piece or equivalent surrounds the tube at the distal end of the tube. A control valve member located near the proximal end of the tube has a vacuum connection member which provides means for connecting the primary conduit to a vacuum. The suction catheter of the present invention is provided with means for providing oxygenated liquid to the secondary conduit. This may be comprised of an oxygen exchanger which is fed by a source of oxygen and a source of irrigating fluid, a Y-connection joining a source of oxygen and a source of irrigating fluid or a catheter connected to a reservoir of irrigating fluid having oxygen bubbled in through it.

Other objects and advantages of the invention will become apparent during the following description of the presently preferred embodiments of the invention taken in conjunction with the drawings.

DETAILED DESCRIPTION OF THE PREFERRED EMBODIMENTS

Figure 1:
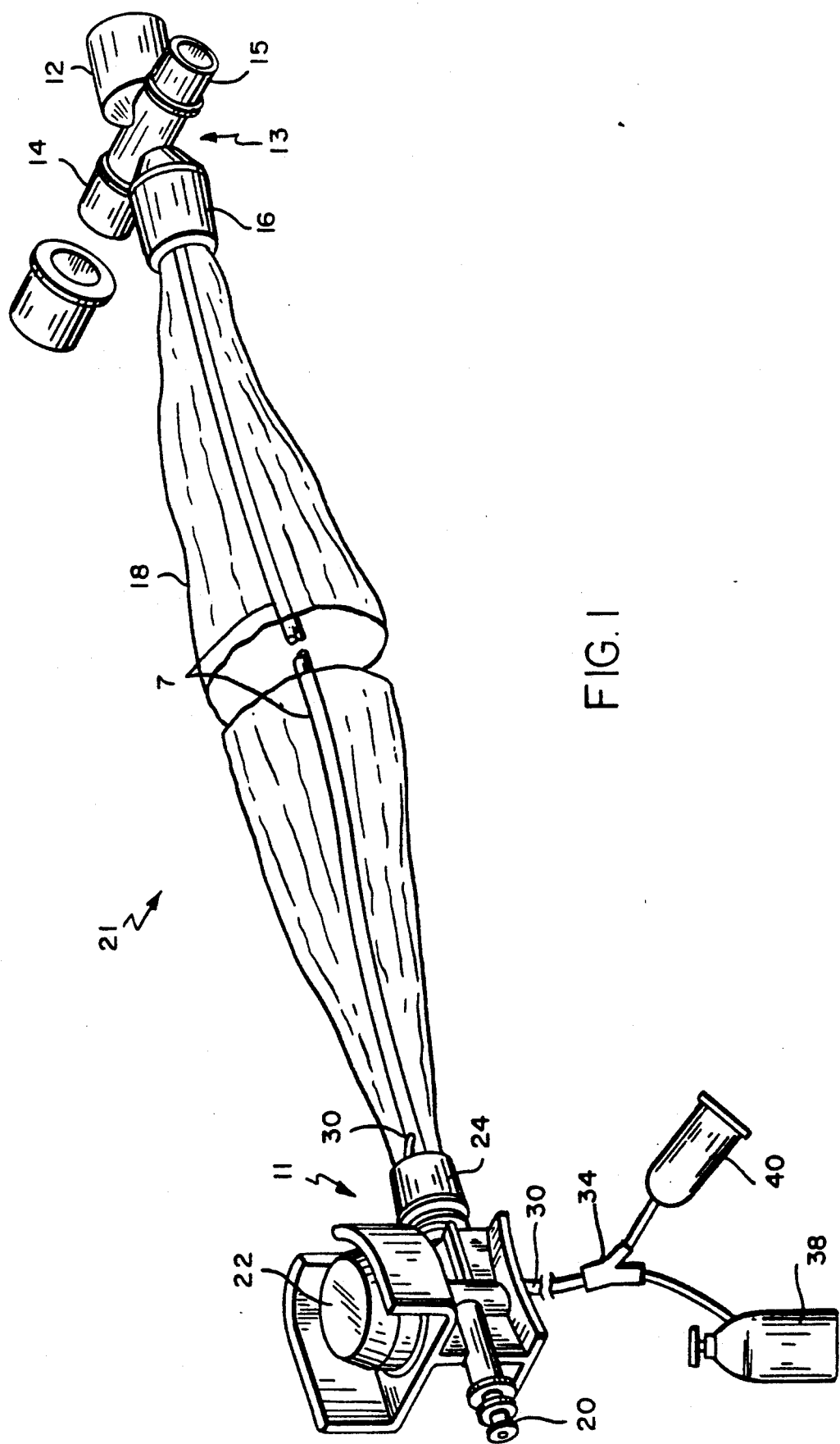
FIG. 1 is a perspective view of a suction catheter of the present invention.

Referring now to the drawings, FIG. 1 illustrates a suction catheter assembly 21 of the present invention. The catheter assembly 21 includes a catheter tube 7 which extends from its proximal end in a control valve 11 which has a vacuum connection member 2 down to its distal end where it either sticks out of or is surrounded by a cross piece member 13. The catheter tube 7 can be slid back and forth through the cross piece 13. The cross piece has an output port 12 which is provided for connnection to a suitable connecting element to a patient, such as an oral and/or nasal connecting element and particularly an endotracheal or tracheostomy connector (not shown). The ports 14 and 15 of the cross piece 13 are provided for connection to a ventilating apparatus (not shown) via a input tube (not shown) and a return tube (not shown) as known in the art. A port 16 extending from the cross piece in the direction of the proximal end of the catheter tube is connected to a protective sleeve 18.

The catheter tube 7, at its distal end, passes through the cross shaped member 13 through a wiper seal located in the extension 16 from the member and surrounding the periphery of the catheter tube. The wiper seal can be made of a silicone rubber material.

The proximal end of the catheter tube is connected to a control valve member 11. The control valve 11 includes a vacuum connection outlet 20 for connection to a vacuum source (not shown). The vacuum connection member 20 includes a bore of the same size as the inside diameter of the conduit in the catheter tube 7 for providing suction. The vacuum connection member 20 is normally made of a relatively rigid material such as SAN (polymer of styrene and acrylonitrile). Also located on the control valve member 11 is the valve member 22. The valve member 22 illustrated is a spool type valve preferably made of butyl rubber. The valve is operated by manually applying a force to the top of the valve rubber member whereby the valve is pushed down such that it no longer blocks the passageway to the catheter tube and thereby suction can be applied from the vacuum source. Upon release of the manual force, the valve returns to its normal resting position in which the vacuum source is sealed from the catheter tube 7. In other embodiments, the valve 11 may be replaced by any suction control member such as an open port valve, a clamp, etc.

The protective sleeve 18 surrounds at least the majority of the length of the catheter tube 7. The protective sleeve 18 is adapted to permit the distal end of the catheter tube to be extended from the protective sleeving to a patient and to be withdrawn from the patient. The flexible protective sleeve is generally cylindrical in shape and is formed of a flexible, lightweight, translucent plastic material such as a high clarity polyethylene with a typical thickness of about 0.002 inches. The ends of the protective sleeve 18 are adhesively secured to the port 16 of the cross piece and at its other end to a collar 24 on the control valve. The connection of the sleeve to the collar 24 and port 16 can be reinforced by threading and twisting the collar 24 or outer ring of the port 16 onto a mating externally threaded tube and locating the end of the protective sleeve 18 and an adhesive between the tube and the outer collar or ring. A typical adhesive is polyvinylchloride doped tetrahydrofuran.

A connector tube 30 is provided for delivering irrigating fluid into the catheter tube 7. The catheter tube 7 is advantageously provided with two conduits. This may be provided by using a dual lumen catheter for catheter tube 7 or inserting a tube within a tube to provide two conduits. The larger conduit of the two is used for the suctioning. The other conduit is used for delivering irrigating fluid into the trachea or other cavity in which the catheter is being used. The connector tube 30 is inserted through the control valve member underneath its collar 24. The connector tube 30 inserts into the catheter tube 7. When the catheter tube 7 is a dual lumen catheter, the connector tube 30 is inserted into one of the conduits in the tube 7. When the catheter tube 7 is a single lumen catheter, the connector tube 30 extends into the catheter tube 7 and extends all the way through the catheter tube 7 to its distal end. The embodiment described above in which the catheter tube 7 is a dual lumen catheter, is known and available as the STERICATH, Model No. 6100 available from Smiths Industries Medical Systems, Inc. (SIMS)

In accordance with the present invention, means are provided for delivering oxygenated irrigating fluid out through the connector tube 30 into the patient for the purpose of lavaging the patient. In accordance with the embodiment of FIG. 1, a Y-connector 34 is connected to the connection tube 30. The Y-connector 34 has two input ends, one of which is connected to a pressurized gas source 38 and the other of which is connected to a source of irrigating fluid 40. Typically, the irrigating fluid is a saline solution. The gas source 38 preferably provides an oxygen containing gas under pressure. The gas source 38 is pressurized so that the oxygen-containing gas when forced out into the Y-connector 34 mixes with the saline solution. Further the pressure can be used as a jet to expel the liquid faster and farther.

Figure 2:
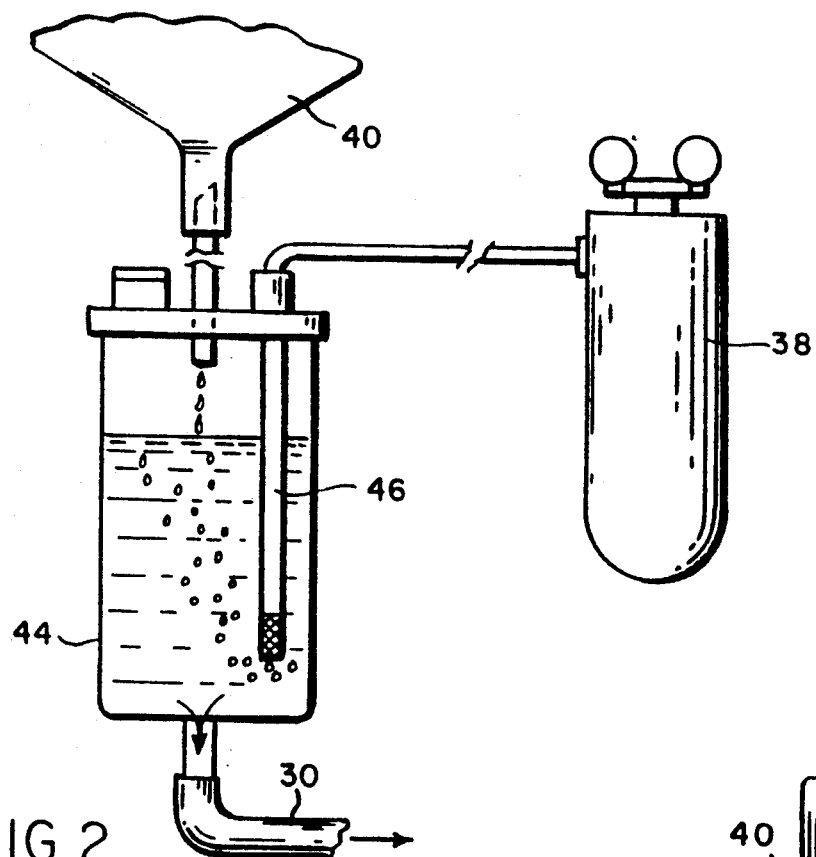
FIG. 2 is an alternate embodiment of the means for providing oxygenated liquid to the suction catheter of the present invention.

Referring now to FIG. 2, an alternate embodiment for providing oxygenated liquid through the connector tube 30 is shown. A reservoir 44 is provided into which the lavage solution is dripped from a fluid source 40. A source of pressurized gas 38 is provided through a bubbling tube 46 into the reservoir 44. Thus, the oxygen from source 38 is bubbled into the reservoir 44 of fluid solution. The bubbling of the oxygen into the solution promotes dissolution of the oxygen in the solution so that the solution provided to the connector tube 30 is oxygenated.

Figure 3:
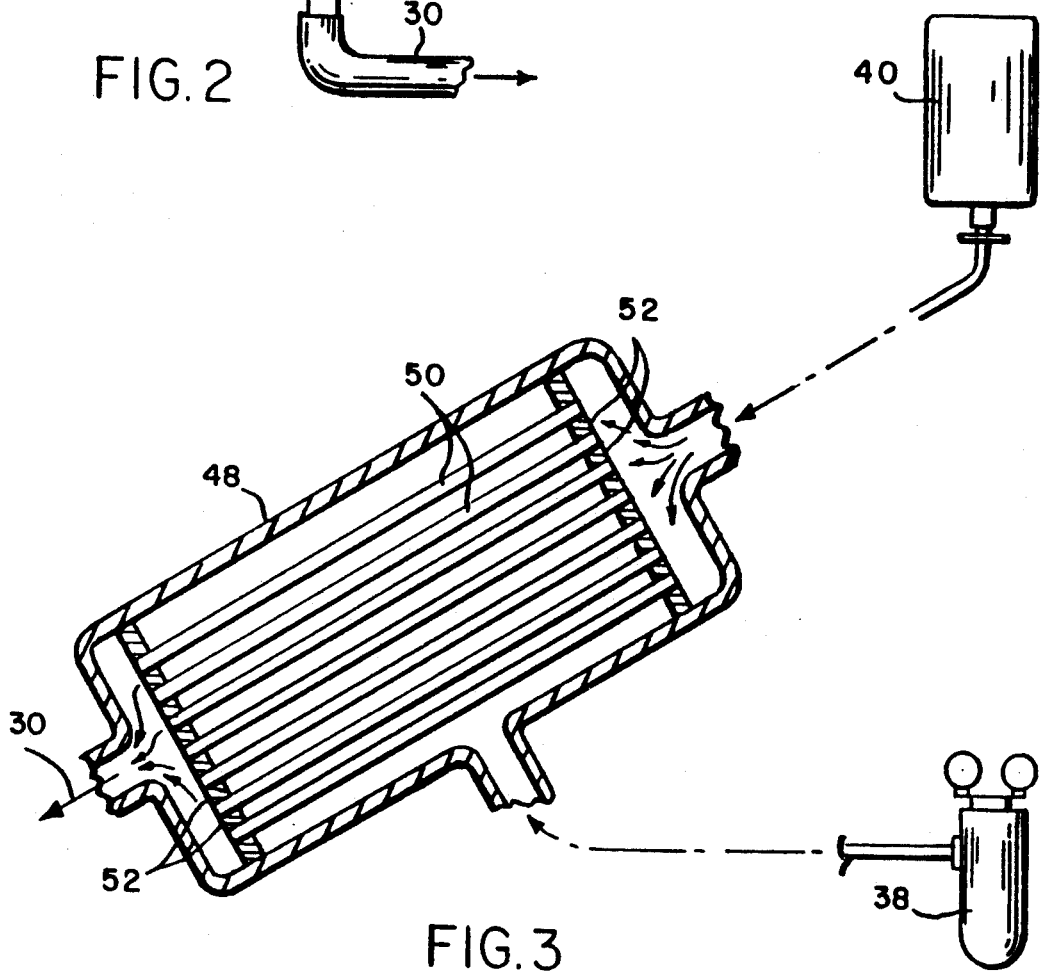
FIG. 3 is a second alternate embodiment of a means for providing oxygenated liquid to the suction catheter of the present invention.

Referring now to FIG. 3, an oxygen exchanger 48 is provided for providing a solution of oxygenated liquid into the connector tube 30. The oxygen exchanger 48 includes a bundle of hollow hydrophobic fibers 50. The opposite ends of the fibers are each encased in a castable polymeric potting 52, such as a polyurethane potting. Fluid from source 40 flows through the hydrophobic fibers 50. Oxygen supplied by source 38 passes through the fibers and oxygenates the fluid. The oxygenated fluid is supplied through the connector tube 30 to the suction catheter.

The suction catheter of the present invention is used by connecting the patient cross piece 13 to the patient and then inserting the catheter tube 7 into the patient cavity, normally the trachea. Oxygen is mixed or dissolved in an irrigating fluid by using either the Y-connector 34, the bubbling reservoir 44 or the oxygen exchanger 48 or any other equivalent means for obtaining oxygenated fluid to expel through the distal end of the catheter tube 7. The irrigating fluid is expelled from the end of the conduit in the patient's lungs so as to dislodge debris such as mucous. A vacuum source attached to the vacuum connection member 20 sucks the dislodged debris and irrigating fluid up through the catheter tube 7 away from the trachea. Advantageously, the oxygen which is removed by the suction of the vacuum source is somewhat replenished by the oxygen dissolved in the irrigating fluid. While this lavaging and suctioning is being performed, the patient respirates with the help of a ventilator connected to the ports 14 and 15 of the cross piece. Thus, while the patient is generally receiving oxygen through respiration, the oxygenated irrigating fluid provides oxygen directly in the area where suctioning is taking place. Thus, the localized loss of oxygen is avoided or at least significantly diminished.

While preferred embodiments for the present invention have been illustrated and described, it will be appreciated that various changes can be made therein without departing from the spirit and scope of the present invention.

We claim:

1. A suction catheter suitable for use in removing undesirable fluid from a patient, said suction catheter comprising:
   a tube having a proximal end and a distal end, said distal end being suitable for insertion into a patient wherein said tube includes a primary conduit for removing fluid from a patient upon application of a vacuum and a secondary conduit for providing liquid for lavaging said patient;
   a cross piece mounted so as to surround said tube in the vicinity of the distal end of said tube;

a suction control means attached to said tube in the vicinity of the proximal end of said tube;

a vacuum connector at the proximal end of said suction control means;

an input tube, connected to said secondary conduit, for providing oxygenated liquid to said secondary conduit; and a reservoir of irrigating fluid connected to said input tube, said reservoir having oxygen bubbled in through said irrigating fluid.

2. A suction catheter suitable for use in removing undesirable fluid from a patient, said suction catheter comprising:

a tube having a proximal end and a distal end, said distal end being suitable for insertion into a patient wherein said tube includes a primary conduit for removing fluid from a patient upon application of a vacuum and a secondary conduit for providing liquid for lavaging said patient;

a cross piece mounted so as to surround said tube in the vicinity of the distal end of said tube;

a suction control means attached to said tube in the vicinity of the proximal end of said tube;

a vacuum connector at the proximal end of said suction control means;

an input tube, connected to said secondary conduit, for providing oxygenated liquid to said secondary conduit;

an oxygen exchanger connected to said input tube;

a source of oxygen connected so as to feed oxygen to said oxygen exchanger; and a source of irrigating fluid connected to feed irrigating fluid to said oxygen exchanger.

3. A suction catheter suitable for use in removing undesirable fluid from a patient, said suction catheter comprising:

a tube having a proximal end and a distal end, said distal end being suitable for insertion into a patient wherein said tube includes a primary conduit for removing fluid from a patient upon application of a vacuum and a secondary conduit for providing liquid for lavaging said patient;

a cross piece mounted so as to surround said tube in the vicinity of the distal end of said tube;

a suction control means attached to said tube in the vicinity of the proximal end of said tube;

a vacuum connector at the proximal end of said suction control means;

an input tube, connected to said secondary conduit, for providing oxygenated liquid to said secondary conduit;

a Y-connector having an output end connected to said input tube and two input ends;

a source of oxygen connected to one of said two input ends of said Y-connector; and a source of irrigating fluid connected to the other of said two input ends of said Y-connector.

4. A method for removing undesired debris from a cavity in a patient comprising the steps of:

inserting a suction catheter into said cavity;

dissolving oxygen in an irrigating fluid solution to produce oxygenated irrigating fluid by bubbling oxygen in a reservoir of irrigating fluid;

delivering the oxygenated irrigating fluid through a first conduit in said catheter to said cavity so as to dislodge debris; and administering a vacuum through a second conduit in said catheter so as to remove dislodged debris and irrigating fluid from said cavity.

5. The method of claim 4 further comprising the step of ventilating said patient during said steps of delivering and administering.

6. A method for removing undesired debris from a cavity in a patient comprising the steps of:

introducing a catheter into said cavity;

feeding an irrigating fluid into one arm of a Y-connector which feeds said irrigating fluid through said catheter;

feeding a gas under pressure into a second arm of said Y-connector to mix said gas with said fluid and to eject said mixture of fluid and gas under force from said catheter and into said cavity; and administering a vacuum in said catheter to remove dislodged debris and irrigating fluid.

7. A method for removing undesired debris from a cavity in a patient comprising the steps of:

inserting a suction catheter into said cavity;

dissolving oxygen in an irrigating fluid solution to produce oxygenated irrigating fluid by feeding oxygen and said irrigating fluid through an oxygen exchanger;

delivering the oxygenated irrigating fluid through a first conduit in said catheter to said cavity so as to dislodge debris; and administering a vacuum through a second conduit in said catheter so as to remove dislodged debris and irrigating fluid from said cavity.

8. A method for removing undesired debris from a cavity in a patient comprising the steps of:

inserting a suction catheter into said cavity;

dissolving oxygen in an irrigating fluid solution to produce oxygenated irrigating fluid by feeding oxygen through one input end of a Y-connector and feeding irrigating fluid through a second input end of the Y-connector;

delivering the oxygenated irrigating fluid through a first conduit in said catheter to said cavity so as to dislodge debris; and administering a vacuum through a second conduit in said catheter so as to remove dislodged debris and irrigating fluid from said cavity.

* * * * *